United States Patent
Zhang

(10) Patent No.: US 9,727,717 B2
(45) Date of Patent: Aug. 8, 2017

(54) MOBILE DEVICE AND PUPIL RECOGNITION METHOD

(75) Inventor: Fan Zhang, Huizhou (CN)

(73) Assignee: HUIZHOU TCL MOBILE COMMUNICATION CO., LTD., Huizhou (CN)

( * ) Notice: Subject to any disclaimer, the term of this patent is extended or adjusted under 35 U.S.C. 154(b) by 492 days.

(21) Appl. No.: 14/112,861

(22) PCT Filed: Jun. 20, 2012

(86) PCT No.: PCT/CN2012/077192
§ 371 (c)(1),
(2), (4) Date: Oct. 18, 2013

(87) PCT Pub. No.: WO2013/010421
PCT Pub. Date: Jan. 24, 2013

(65) Prior Publication Data
US 2014/0033301 A1    Jan. 30, 2014

(30) Foreign Application Priority Data

Jul. 18, 2011 (CN) .......................... 2011 1 0200966

(51) Int. Cl.
*G11C 7/00* (2006.01)
*G06F 17/30* (2006.01)
(Continued)

(52) U.S. Cl.
CPC ............ *G06F 21/32* (2013.01); *A61B 3/0025* (2013.01); *A61B 3/0033* (2013.01); *A61B 3/11* (2013.01);
(Continued)

(58) Field of Classification Search
CPC ............................. G06F 21/32; H04L 63/0861
(Continued)

(56) References Cited

U.S. PATENT DOCUMENTS 6,120,461 A * 9/2000 Smyth ................... A61B 3/113
348/E13.041
6,267,477 B1 * 7/2001 Karpol ................. A61B 3/1225
351/221
(Continued)

FOREIGN PATENT DOCUMENTS

CN    101369311 A    2/2009
CN    201204614 Y    3/2009
(Continued)

OTHER PUBLICATIONS

Glen A. Myers; Microcomputer-Based Instrument Uses an Interial Model to Track the Eye; 1991; IEEE; p. 14-20.*
(Continued)

*Primary Examiner* — Monjour Rahim
(74) *Attorney, Agent, or Firm* — Shimokaji IP

(57) ABSTRACT

A mobile device comprises a pupil information collecting module and a master control module, such that the pupil information collecting module may be used for collecting pupil characteristic information of a user. The master control module may receive the pupil characteristic information of the user when the user accesses a controlled unit, and may determine, on the basis of the pupil characteristic in formation of the user, if the user is allowed to access the controlled unit. The mobile device may use the pupil characteristic information of the user to perform identity verification.

20 Claims, 4 Drawing Sheets

(51) Int. Cl.
*G06F 13/00* (2006.01)
*G06F 12/14* (2006.01)
*G06F 12/00* (2006.01)
*G06F 7/04* (2006.01)
*G06F 21/32* (2013.01)
*G06K 9/00* (2006.01)
*A61B 3/11* (2006.01)
*A61B 3/00* (2006.01)

(52) U.S. Cl.
CPC .. *G06K 9/00597* (2013.01); *F04C 2270/0421* (2013.01)

(58) Field of Classification Search
USPC .......................................................... 726/19
See application file for complete search history.

(56) References Cited

U.S. PATENT DOCUMENTS

| | | | | |
|---|---|---|---|---|
| 2006/0291702 A1* | 12/2006 | Miessbacher | ........ | G06K 9/0061 382/117 |
| 2007/0014552 A1* | 1/2007 | Ebisawa | ............ | G06K 9/00604 396/51 |
| 2007/0171362 A1* | 7/2007 | Simpson | ............... | A61F 2/1654 351/159.11 |
| 2007/0288759 A1* | 12/2007 | Wood | .................... | G06Q 20/341 713/186 |
| 2009/0016574 A1* | 1/2009 | Tsukahara | .............. | A61B 5/117 382/117 |
| 2010/0310133 A1* | 12/2010 | Mason | .................... | A61B 5/117 382/117 |
| 2011/0231007 A1* | 9/2011 | Biehle | ................... | G06Q 10/087 700/218 |

FOREIGN PATENT DOCUMENTS

| | | |
|---|---|---|
| CN | 201352825 Y | 11/2009 |
| JP | 2009211597 A | 9/2009 |

OTHER PUBLICATIONS

Zhao-Bang Pu, et al., Development and Application of Iris Recognition Technology, Optics and Precision Engineering, Jun. 2004, p. 316-322, vol. 12, No. 3.

* cited by examiner

MOBILE DEVICE AND PUPIL RECOGNITION METHOD

TECHNICAL FIELD

The present invention relates to a mobile device and, in particular, relates to a mobile device using a pupil characteristic information of a user to perform identity verification.

BACKGROUND

An existing mobile device, such as a mobile phone, may have all its functions and files displayed on a screen after startup. As for a file or program which can only be accessed with a corresponding authorization, a password may be set for it. However this kind of encryption may have a relatively lower security level.

The patent "Method for Realizing Related Mobile Communication Terminal Function by Fingerprint Recognition" (Application No.: 200910200922.6) discloses a security protection method using fingerprint recognition. Although the fingerprint recognition may be unique, it may still be risky because a fingerprint may be easily stolen due to fingers touching many things in daily life.

SUMMARY OF THE INVENTION

A technical solution employed in an embodiment of the present invention to solve the above mentioned technical issue is: providing a mobile device, which comprises a pupil information collecting module and a master control module; the pupil information collecting module comprises: a pupil scanner for collecting pupil characteristic information of a user; a driver for driving the pupil scanner to collect the pupil characteristic information of the user; a microprocessor for controlling the pupil scanner and the driver, calculating the pupil characteristic information and sending it to the master control module; the master control module receives the pupil characteristic information of the user when the user accesses a controlled unit and determines, on the basis of the pupil characteristic information of the user, if the user is allowed to access to the controlled unit; the controlled unit comprises system programs, applications or files of the mobile device, and the pupil characteristic information comprises the distance between the pupil and the pupil scanner, the pupil luminance, the curvature of the pupil lens, and the lines of the pupil capillaries.

According to an embodiment of the present invention, the pupil scanner comprises: an ultrasonic transmitting and receiving unit for acquiring the distance between the pupil and the pupil scanner; a photosensitive diode for collecting the pupil luminance; a laser emission unit for providing an illumination source to facilitate the photosensitive diode to collect the pupil luminance; a signal processing unit for optimizing the signals collected by the photosensitive diode; an interface unit for connecting the ultrasonic transmitting/receiving unit, and the photosensitive diode and the laser emission unit to the microprocessor.

According to an embodiment of the present invention, the signal processing unit comprises at an amplifier and a filter. A technical solution employed in the present invention to solve above mentioned technical issue is: providing a mobile device, which comprises: a pupil information collecting module for collecting pupil characteristic information of a user; a master control module for receiving the pupil characteristic information of the user when the user accesses a controlled unit, which determines, on the basis of the pupil characteristic information of the user, if the user is allowed to access the controlled unit. According to an embodiment of the present invention, the controlled unit comprises system programs, applications or files of the mobile device.

According to an embodiment of the present invention, the pupil information collecting module comprises: a pupil scanner for collecting the pupil characteristic information of the user; a driver for driving the pupil scanner to collect the pupil characteristic information of the user; a microprocessor, for controlling the pupil scanner and the driver, and calculating the pupil characteristic information and sending it to the master control module.

According to an embodiment of the present invention, the pupil characteristic information comprises the distance between the pupil and the pupil scanner, the pupil luminance, the curvature of the pupil lens, and the lines of the pupil capillaries.

According to an embodiment of the present invention, the pupil scanner comprises: an ultrasonic transmitting/receiving unit for acquiring the distance between the pupil and the pupil scanner; a photosensitive diode for collecting the pupil luminance; a laser emission unit for providing an illumination source to facilitate the collecting of the pupil luminance by the photosensitive diode; a signal processing unit for optimizing the signals collected by the photosensitive diode; an interface unit for connecting the ultrasonic transmitting/receiving unit, the photosensitive diode and the laser emission unit to the microprocessor.

According to an embodiment of the present invention, the signal processing unit comprises an amplifier and a filter.

Another technical solution employed in the present invention in order to solve the above mentioned technical issue is: providing a pupil recognition method for a mobile device, which comprises the steps of: setting pupil recognition for a controlled unit of the mobile device; collecting pupil characteristic information of a user able to access the controlled unit by using the pupil information collecting module of the mobile device; and setting an access authorization for the pupil characteristic information of the user by using the master control module of the mobile device.

According to an embodiment of the present invention, when using the pupil information collecting module to collect the pupil characteristic information of the user to access the controlled unit, if the collected pupil characteristic information is found to be unmatched with a requirement, then the user is prompted to perform collection again until the pupil characteristic information matching the requirement is collected, and the pupil characteristic information matching the requirement is stored in the internal memory.

According to an embodiment of the present invention, the user accessing the controlled unit of the mobile device comprises the following steps: prompting the user to perform identity verification; collecting the pupil characteristic information of the user by the pupil information collecting module; comparing the collected pupil characteristic information of the user with the pupil characteristic information stored in the internal memory by the master control module to determine if the pupil characteristic information is one that is allowed to access the controlled unit, and if yes, then granting the access; otherwise denying the access.

According to an embodiment of the present invention, when the pupil information collecting module collects the pupil characteristic information of the user, it comprises following steps: resetting the pupil information collecting module; driving the pupil scanner by the driver to collect the pupil characteristic information of the user; determining by using the microprocessor if the pupil characteristic information collecting is finished; if yes, calculating the pupil characteristic information collected by the pupil scanner and sending it to the master control module, and if not, then continuously driving the pupil scanner to perform collection.

The mobile device and the pupil recognition method disclosed in the present invention may perform identity verification through the pupil characteristic information of the user, providing security.

Described above is the summary of the technical solutions of the present invention, which can be implemented in order to understand the technical means of the present invention more clearly, and the present invention may be further described with reference to the embodiments and the accompanied drawings for a better understanding of the above mentioned purposes and other purposes, characters and advantages of the present invention.

DETAILED DESCRIPTION OF THE INVENTION

The present invention will be further described in detail with the accompanied drawings and embodiments.

Figure 1:
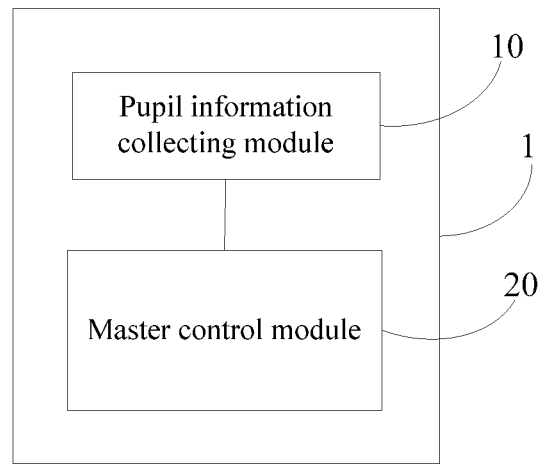
FIG. 1 is a schematic diagram showing the module structure of a mobile device according to an embodiment of the present invention.

Referring to FIG. 1, the present invention provides a mobile device 1, such as a mobile phone or a PDA. The mobile device 1 comprises a pupil information collecting module 10 and a master control module 20, wherein the pupil information collecting module 10 is used to collect the pupil characteristic information of a user; the master control module 20 receives the pupil characteristic information of the user when the user accesses a controlled unit, and determines, on the basis of the pupil characteristic information of the user, if the user is allowed to access the controlled unit. In an embodiment of the present invention, the controlled unit comprises system programs, applications or files of the mobile device 1.

Figure 2:
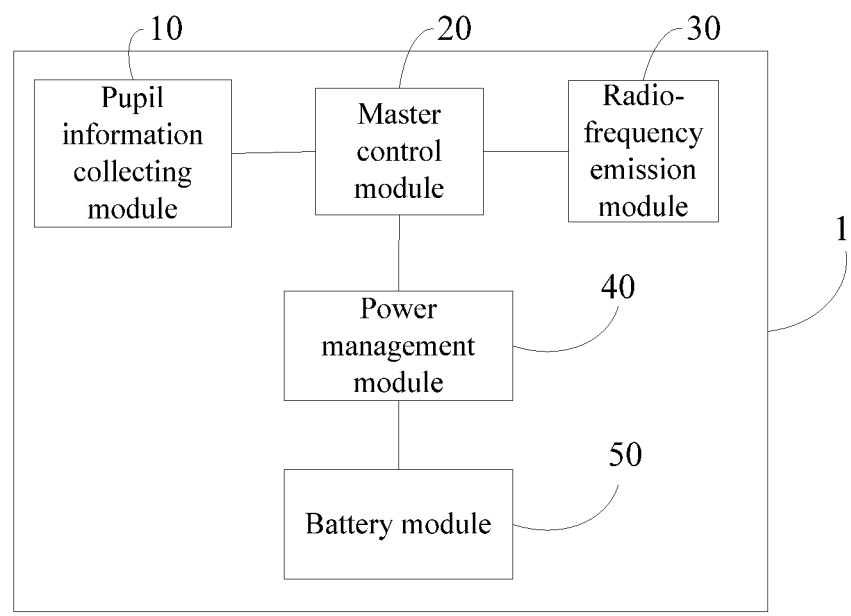
FIG. 2 is a schematic diagram showing the module structure of a mobile device according to another embodiment of the present invention.

Referring to FIG. 2, in another embodiment of the present invention, the mobile device 1 comprises a pupil information collecting module 10, a master control module 20, a radio-frequency emission module 30, a power management module 40 and a battery module 50, wherein the radio-frequency emission module 30 is used to communicate with an external network, the power management module 40 is used to divide the voltage of the battery module 50 to each function module, and the battery module 50 is used to provide the power for the system to work.

Figure 3:
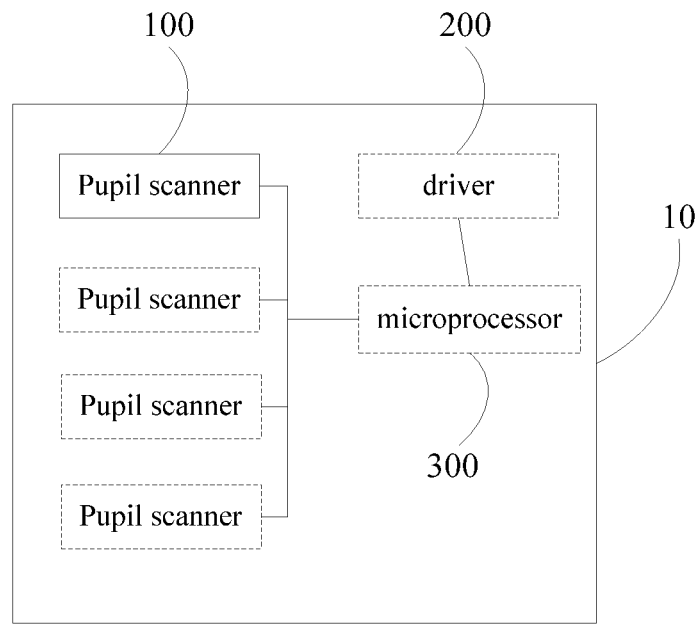
FIG. 3 is a schematic diagram showing the module structure of the pupil information collecting module shown in FIG. 1.

Referring to FIG. 3, in an embodiment of the present invention, the pupil information collecting module 10 mainly comprises a pupil scanner 100, a driver 200 and a microprocessor 300.

The pupil scanner 100 may be used to collect the pupil characteristic information of a user; responding to the order of the microprocessor 300, the driver 200 may be used to drive an array of the pupil scanner 100 to multiple positions to collect the pupil characteristic information in the corresponding positions, and the driver 200 can be a motor, etc.; the microprocessor 300 may be used to control the pupil scanner 100 and the driver 200, calculate the pupil characteristic information and send it to the master control module 20.

In an embodiment of the present invention, the pupil characteristic information comprises the distance between the pupil and the pupil scanner 100, the pupil luminance, the curvature of the pupil lens, and the lines of the pupil capillaries.

Figure 4:
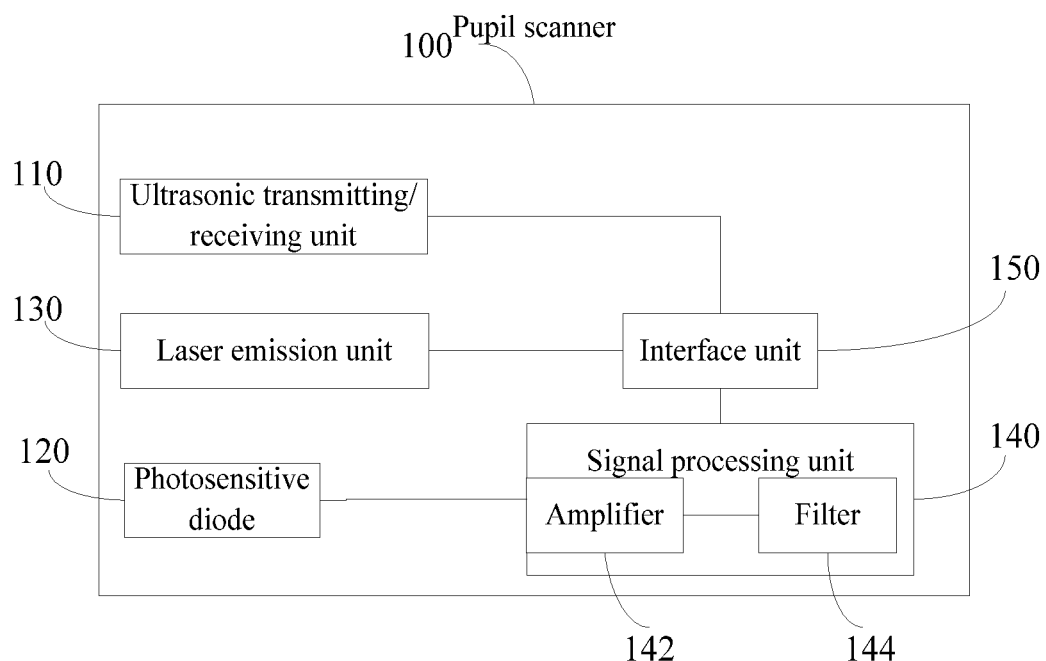
FIG. 4 is a schematic diagram showing the module structure of the pupil scanner shown in FIG. 3.

Referring to FIG. 4, in an embodiment of the present invention, the pupil scanner 100 further comprises an ultrasonic transmitting/receiving unit 110, a photosensitive diode 120, a laser emission unit 130, a signal processing unit 140 and an interface unit 150.

The ultrasonic transmitting/receiving unit 110 may be used for acquiring the distance between the pupil and the pupil scanner 100; the photosensitive diode 120 may be used for collecting the luminance of the pupil; the laser emission unit 130 may be used for providing an illumination source to facilitate the photosensitive diode 120 to collect the pupil luminance; the signal processing unit 140 may be used for optimizing the signals collected by the photosensitive diode 120. In an embodiment, the signal processing unit 140 comprises an amplifier 142 for amplifying weak signals of the photosensitive diode 120 and a filter 144 for performing band-pass filtering on collected and amplified noises; the interface unit 150 may be used for connecting the ultrasonic transmitting/receiving unit 110, the photosensitive diode 120 and the laser emission unit 130 to the microprocessor 300.

The pupil recognition method of the mobile device 1 provided by an embodiment of the present invention will be introduced with reference to the above mentioned hardware descriptions.

Figure 5:
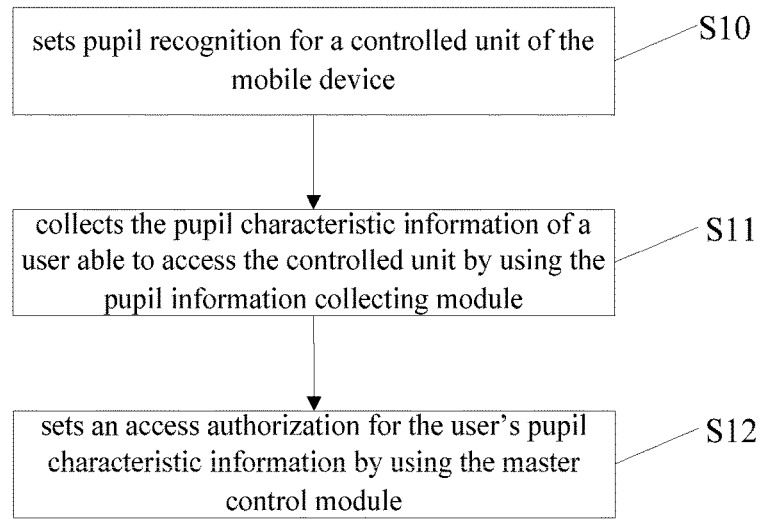
FIG. 5 is a flow diagram of setting a pupil recognition method for a mobile device according to an embodiment of the present invention.

FIG. 5 shows the flow diagram for the pupil recognition method, which comprises the following steps:

S10: setting pupil recognition for a controlled unit of the mobile device 1, such as applying the pupil recognition to a system program (startup program) of the mobile device 1, or to a dedicated application or an important file of the mobile device 1;

S11: collecting the pupil characteristic information of a user able to access the controlled unit by using the pupil information collecting module 10 of the mobile device 1;

S12: setting an access authorization for the pupil characteristic information of the user by using the master control module 20 of the mobile device 1. The access type depends on a specific application circumstance, for example, an ordinary user may have a read only permission, while a special user may have modification permission.

In order to collect the pupil characteristic information of the user accurately, when using the pupil information collecting module 10 to collect the pupil characteristic information of the user able to access the controlled unit, if the collected pupil characteristic information is found to be unmatched with the requirement, then the user may be prompted to perform collection again until the pupil characteristic information matching with the requirement is collected, and then the pupil characteristic information matching with the requirement may be stored in the internal memory.

Figure 6:
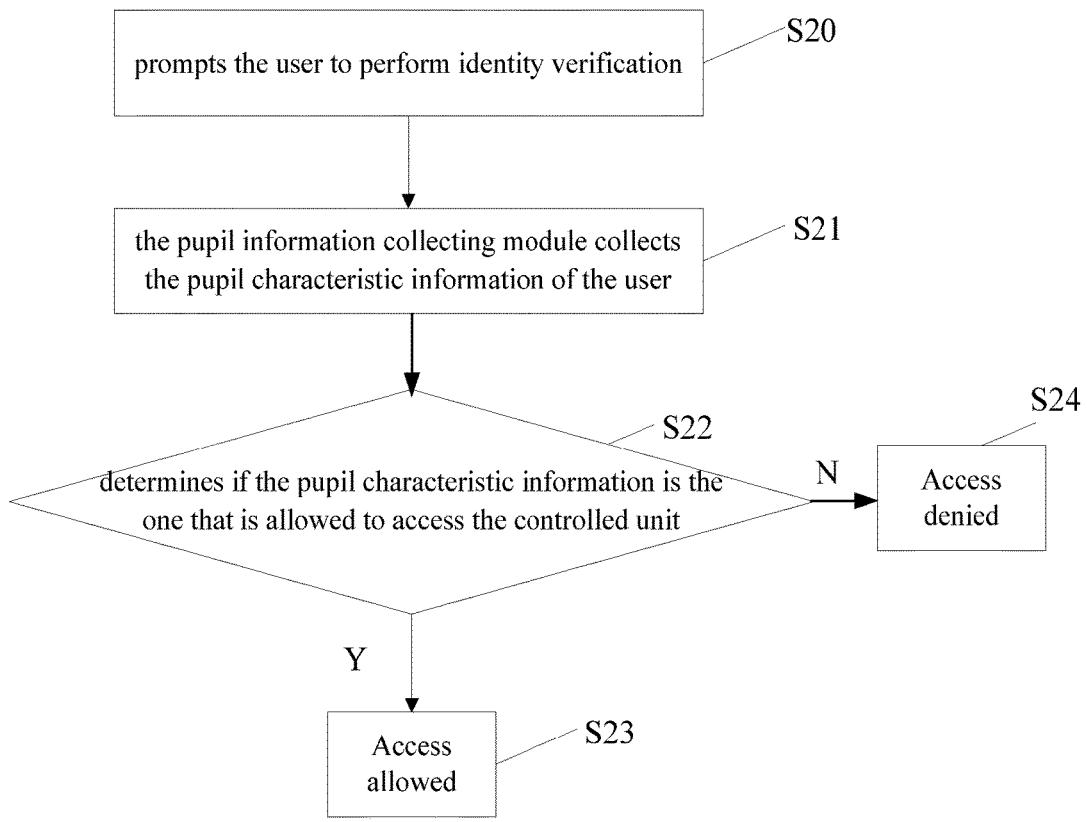
FIG. 6 is a flow diagram showing the user accessing a controlled unit in the mobile device.

FIG. 6 shows a flow diagram of a user accessing a controlled unit in mobile device 1, which comprises the following steps:

S20: prompting the user to perform identity verification, for instance, popping up a verification interface on the display screen (not shown) of the mobile device 1;

S21: the pupil information collecting module 10 collecting the pupil characteristic information of the user;

S22: the master control module 20 comparing the collected pupil characteristic information of the user with the pupil characteristic information stored in the internal memory to determine if the pupil characteristic information is the one that is allowed to access the controlled unit;

S23: if yes, then granting the access;

S24: if not, then denying the access.

Figure 7:
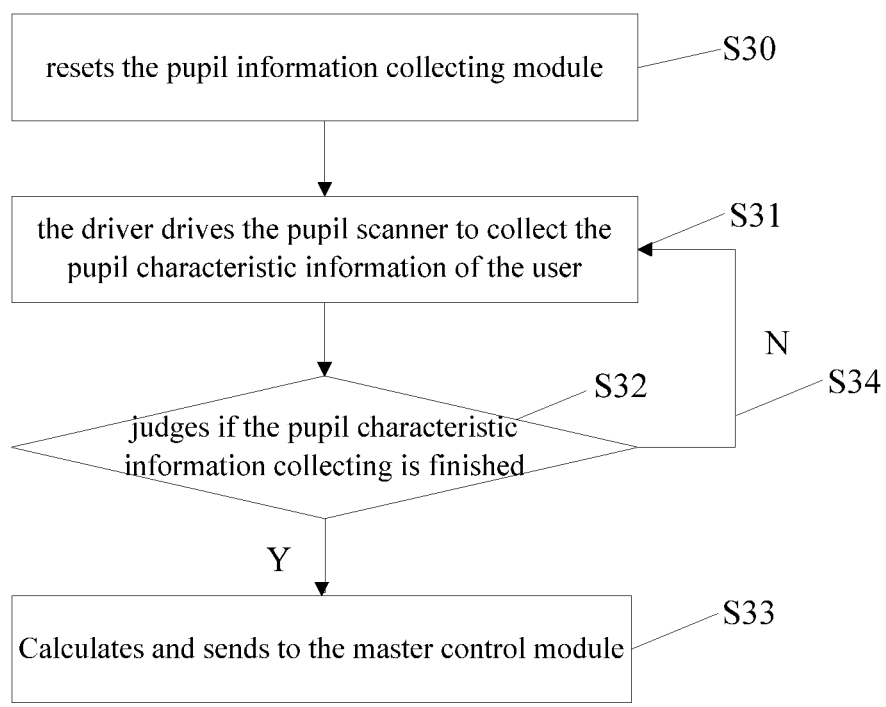
FIG. 7 is a work flow diagram showing the pupil information collecting module collecting the pupil characteristic information.

FIG. 7 is a work flow diagram of the pupil information collecting module 10 collecting the pupil characteristic information of the user, which comprises the following steps:

S30: resetting the pupil information collecting module 10, that is, the driver 200 drives the pupil scanner 100 to the initial position;

S31: the driver 200 driving the array of the pupil scanner 100 to multiple positions to collect the pupil characteristic information of the user in corresponding positions, that is, acquiring the distance between the pupil and the pupil scanner 100 by the ultrasonic transmitting/receiving unit 110, and collecting the luminance of the pupil by the photosensitive diode 120;

S32: the microprocessor 300 determining if the pupil characteristic information collecting is finished, by determining if the driver 200 reaches the final position. If the driver 200 does not reach the final position, then the microprocessor 300 making the driver 200 continuously drives the pupil scanner 100 to collect the pupil characteristic information of the user;

S33: if the pupil characteristic information collecting has been finished, that is, the driver 200 has reached the final position, then calculating the pupil characteristic information collected by the pupil scanner 100 and sending it to the master control module, such as calculating three dimension information such as the curvature of the pupil lens, the capillary lines of the pupil and the cornea thickness through the parameters such as the distance between the pupil and the pupil scanner 100 and the luminance of the pupil; and S34: if not finished, then continuing step S31.

It is easy for those skilled in the field to understand that the mobile device and the pupil recognition use the pupil characteristic information of a user to perform the identity verification, as the pupil characteristic information of the user is unique, and may not be stolen by others, thus providing security.

Described above are embodiments of the present invention for illustrative purpose rather than limiting the scope of the present invention. All equivalent structure or process changes made according to the description and accompanied drawings of the present invention, or direct or indirect applications in other related fields, should fall into the protective scope of the present invention.

The invention claimed is:

1. A mobile device, comprising:
a pupil information collecting module; and
a master control module,
wherein the pupil information collecting module comprises:
a pupil scanner for collecting pupil characteristic information of a user;
a driver for driving the pupil scanner to collect the pupil characteristic information of the user;
a microprocessor for controlling the pupil scanner and the driver, calculating the pupil characteristic information and sending it to the master control module,
wherein the master control module receives the pupil characteristic information of the user when the user accesses a controlled unit, and determines, on the basis of the pupil characteristic information of the user, if the user is allowed to access the controlled unit by verifying the user's identity, and
wherein the controlled unit comprises system programs, applications or files of the mobile device, and
wherein the pupil characteristic information calculated by the microprocessor comprises a curvature of a pupil lens which is an internal focusing element of the pupil curved on both sides, wherein the curvature of the pupil lens is used to verify the user's identity.

2. The mobile device according to claim 1, wherein, the pupil scanner comprises:
an ultrasonic transmitting/receiving unit for acquiring a distance between a pupil and a pupil scanner;
a photosensitive diode for collecting a pupil luminance;
a laser emission unit for providing an illumination source to facilitate the photosensitive diode collecting the pupil luminance;
a signal processing unit for optimizing signals collected by the photosensitive diode;
an interface unit connecting the ultrasonic transmitting/receiving unit, the photosensitive diode and the laser emission unit to a microprocessor.

3. The mobile device according to claim 2, wherein the signal processing unit comprises an amplifier and a filter.

4. A mobile device, comprising:
a pupil information collecting module for collecting pupil characteristic information of a user, comprising a microprocessor for calculating pupil characteristic information collected;
a master control module for receiving the pupil characteristic information of the user when the user accesses a controlled unit, and the master control module is configured to determine, based on the pupil characteristic information of the user, if the user is allowed to access the controlled unit, wherein the pupil characteristic information comprises the curvature of the pupil lens.

5. The mobile device according to claim 4, wherein the controlled unit comprises system programs, applications or files of the mobile device.

6. The mobile device according to claim 5, wherein the pupil information collecting module comprises:
a pupil scanner for collecting the pupil characteristic information of the user; and
a driver for driving the pupil scanner to collect the pupil characteristic information of the user,
wherein the microprocessor controls the pupil scanner and the driver, and after collecting, calculating the pupil characteristic information and sending it to the master control module.

7. The mobile device according to claim 6, wherein the pupil characteristic information comprises a distance between a pupil and the pupil scanner, a pupil luminance, and a curvature of the pupil lens.

8. The mobile device according to claim 7, wherein the pupil scanner comprises:
an ultrasonic transmitting/receiving unit for obtaining the distance between the pupil and the pupil scanner;
a photosensitive diode for collecting the pupil luminance;
a laser emission unit for providing an illumination source to facilitate the collecting of the pupil luminance by the photosensitive diode;
a signal processing unit for optimizing a plurality of signals collected by the photosensitive diode; and
an interface unit for connecting the ultrasonic transmitting/receiving unit, the photosensitive diode and the laser emission unit to the microprocessor.

9. The mobile device according to claim 8 wherein the signal processing unit comprises an amplifier and a filter.

10. A pupil recognition method for a mobile device, comprising:
setting pupil recognition for a controlled unit of the mobile device;
collecting the pupil characteristic information of a user able to access the controlled unit by using a pupil information collecting module of the mobile device comprising a microprocessor;
calculating, by the microprocessor, a cornea thickness of the cornea which is an outermost layer of the pupil; and
setting an access authorization for the pupil characteristic information of the user by using a master control module of the mobile device, wherein the pupil characteristic information comprises a curvature of the pupil lens.

11. The pupil recognition method for a mobile device according to claim 10, wherein, when using the pupil information collecting module to collect the pupil characteristic information of the user that is able to access the controlled unit, if the collected pupil characteristic information is found to be unmatched with an access requirement, then the user is prompted to perform collection again until the pupil characteristic information matching with the access requirement is collected, and the pupil characteristic information matching with the access requirement is stored in the internal memory.

12. The pupil recognition method for a mobile device according to claim 11, wherein, when the user accesses the controlled unit of the mobile device, the method further comprises:
prompting the user to perform identity verification;
collecting the pupil characteristic information of the user by the pupil information collecting module; and
comparing the collected pupil characteristic information of the user with the pupil characteristic information stored in the internal memory by the master control module to determine if the pupil characteristic information is one that is allowed to access the controlled unit, and if yes, then granting the access;
otherwise denying the access.

13. The pupil recognition method for a mobile device according to claim 12, wherein when the pupil information collecting module collects the pupil characteristic information of the user, the method further comprises:
resetting the pupil information collecting module;
driving a pupil scanner by a driver to collect the pupil characteristic information of the user; and
determining by the microprocessor if the pupil characteristic information collecting is finished, and if yes, calculating the pupil characteristic information collected by the pupil scanner and sending it to the master control module, and if not, then continuously driving the pupil scanner to perform collection.

14. The mobile device of claim 1, further comprising:
a radio-frequency emission module for communicating with a network external to the mobile device.

15. The mobile device of claim 4, further comprising:
a radio-frequency emission module for communicating with a network external to the mobile device.

16. The method of claim 10, further comprising:
communicating with a network external to the mobile device using a radio frequency.

17. The mobile device of claim 1, further comprising:
a power management module for dividing a battery voltage between the pupil information collecting module and the master control module.

18. The mobile device of claim 4, further comprising:
a power management module for dividing a battery voltage between the pupil information collecting module and the master control module.

19. The method of claim 10, further comprising:
dividing power from a battery between the steps of setting pupil recognition, collecting the pupil characteristic information of the user, and setting an access authorization for the pupil characteristic information.

20. The method of claim 10, further comprising calculating capillary lines of the pupil of the user.

* * * * *